(12) United States Patent
Daffre et al.

(10) Patent No.: US 7,723,468 B2
(45) Date of Patent: May 25, 2010

(54) ANTIMICROBIAL PEPTIDE, COMPOSITIONS, AND USES THEREFOR

(75) Inventors: Sirlei Daffre, São Paulo (BR); Pedro Ismael Da Silva, Jr., São Paulo (BR); Philippe Bulet, Strasbourg-Cedex (FR)

(73) Assignee: De Sao Paulo Universida de, Sao Paulo (BR)

( * ) Notice: Subject to any disclaimer, the term of this patent is extended or adjusted under 35 U.S.C. 154(b) by 30 days.

(21) Appl. No.: 11/432,286

(22) Filed: May 10, 2006

(65) Prior Publication Data

US 2006/0276380 A1    Dec. 7, 2006

Related U.S. Application Data

(63) Continuation-in-part of application No. 10/296,853, filed as application No. PCT/BR01/00070 on May 29, 2001, now abandoned.

(30) Foreign Application Priority Data

May 29, 2000    (BR) .................................... 0001870

(51) Int. Cl.
    *A61K 38/00* (2006.01)
    *C07K 14/00* (2006.01)
(52) U.S. Cl. .......................................... 530/300; 514/2
(58) Field of Classification Search ....................... None
    See application file for complete search history.

*Primary Examiner*—Anand U Desai
(74) *Attorney, Agent, or Firm*—Paul Davis; Goodwin Procter LLP (57) ABSTRACT

The invention refers to small peptides with low hemolytic activity, presenting similar antiparasitic, antifungal and antibacterial activities.

More specifically, it refers to a peptide called gomesin, with 18 amino acid residues, configured as a hairpin structure consisting of two anti-parallel beta-folded sheets joined by a beta turn, containing four invariable residues of cysteine forming two disulphide bridges, configurable as a cyclic chain with open or closed ends.

10 Claims, 5 Drawing Sheets

FIGURE 1

MIC = Minimum Inhibitory Concentration (µM)

| Microorganism | GOMESIN | |
|---|---|---|
| | amidated | non-amidated |
| | SEQ ID No 1 | SEQ ID No 2 |
| | EXAMPLE 1 | EXAMPLE 2 |
| Gram-positive bacteria | | |
| *Aerococcus viridans* | 0.8-1.6 | 0.8-1.6 |
| *Bacillus cereus* | 6.25-12.5 | 12.5-25 |
| *Bacillus megaterium* | 0.2-0.4 | 0.4-0.8 |
| *Bacillus thuringiensis* | 1.6-3.15 | 3.15-6.25 |
| *Enterococcus faecalis* | 6.2-12.5 | n.m. |
| *Listeria monocytogenes* | 0.8-1.6 | 3.15-6.25 |
| *Micrococcus luteus* | 0.4-0.8 | 0.4-0.8 |
| *Pediococcus acidolactici* | 3.15-6.25 | 3.15-6.25 |
| *Staphylococcus aureus* | 1.6-3.15 | 3.15-6.25 |
| *Staphylococcus epidermidis* | 0.8-1.6 | 3.15-6.25 |
| *Staphylococcus haemolyticus* | 0.8-1.6 | 1.6-3.15 |
| *Staphylococcus saprophyticus* | 0.8-1.6 | 1.6-3.15 |
| *Streptococcus pyogenes* | 1.6-3.15 | 3.15-6.25 |
| *Nocardia asteroides* | 1.6-3.15 | 3.15-6.25 |
| Gram-negative bacteria | | |
| *Agrobacterium tumefaciens* | n.d. | n.d. |
| *Alcaligenes faecalis* | >100 | n.m. |
| *Escherichia coli* 1106 | 0.8-1.6 | 1.6-3.15 |
| *Escherichia coli* D22 | 0.4-0.8 | 0.4-0.8 |
| *Escherichia coli* D31 | 0.8-1.6 | 0.8-1.6 |

FIGURE 1 (cont'd)

| | | |
|---|---|---|
| Escherichia coli SBS363 | 0.4-0.8 | 0.4-0.8 |
| Erwinia carotovora carotovora | 3.15-6.25 | 3.15-6.25 |
| Enterobacter cloacae β12 | 3.15-6.25 | 6.25-12.5 |
| Klebsiella pneumoniae | 3.15-6.25 | 6.25-12.5 |
| Pseudomonas aeruginosa | 1.6-3.15 | 1.6-3.15 |
| Salmonella thyphimurium | 0.8-1.6 | 0.8-1.6 |
| Serratia marcescens Db11 | n.d. | n.d. |
| Xhantomonas campestris pv orizae | 3.15-6.25 | 6.25-12.5 |
| Fungi | | |
| Alternaria brassicola | 0.4-0.8 | 0.4-0.8 |
| Aspergillus fumigatus | 1.6-3.15 | 1.6-3.15 |
| Beauveria bassiana | 12.5-25 | 25-50 |
| Fusarium culmorum | 0.4-0.8 | 0.4-0.8 |
| Fusarium oxysporum | 0.4-0.8 | 0.8-1.6 |
| Neurospora crassa | 0.4-0.8 | 0.4-0.8 |
| Nectria haematococca | 0.2-0.4 | 0.2-0.4 |
| Tricoderma viridae | 0.4-0.8 | 0.4-0.8 |
| Tricophyton mentagrophytes | 0.8-1.6 | 0.8-1.6 |
| Yeast | | |
| Candida albicans | 0.15-0.3 | 0.15-0.3 |
| Candida glabrata | 12.5-25 | 12.5-25 |
| Candida tropicalis | 3.15-6.25 | n.m. |
| Cryptococcus neoformans | 0.8-1.6 | n.m. |
| Saccharomyces cerevisiae | 1.6-3.15 | 1.6-3.15 |

| Peptides | Sequences | MIC | | |
|---|---|---|---|---|
| | | Gram + bacteria | Gram - bacteria | Yeast |
| | | *M. luteus* | *E. coli* | *C. albicans* |
| Gomesin (Gm) | ZCRRLCYKQRCVTYCRGRa | 0.16-0.32 | 0.32-0.64 | 0.32-0.64 |
| D-Gm | zcrrlcykqrcvtycrGra | 0.16-0.32 | 0.32-0.64 | 0.32-0.64 |
| Head-to-tail cyclic Gm | QCRRLCYKQRCVTYCRGR | 0.16-0.32 | 0.32-0.64 | 0.32-0.64 |
| Bicyclo(2-15,6-11)[Cys$^{2,15}$,Asp$^6$,Orn$^{11}$]-Gm | ZCRRLCYKQRCVTYCRGRa | 0.32-0.64 | 0.64-1.28 | 0.64-1.28 |
| Bicyclo(2-15,6-11)[Glu$^2$,Cys$^{6,11}$,Lys$^{15}$]-Gm | ZERRLCYKQRCVTYKRGRa | 0.32-0.64 | 0.64-1.28 | 0.64-1.28 |
| Bicyclo(2-15,6-11)[Asp$^2$,Cys$^{6,11}$,Orn$^{15}$]-Gm | ZDRRLCYKQRCVTYORGRa | 0.32-0.64 | 0.64-1.28 | 0.64-1.28 |
| Bicyclo(2-15,6-11)[Asp$^2$,Cys$^{6,11}$,Dap$^{15}$]-Gm | ZDRRLCYKQRCVTYBRGRa | 0.64-1.28 | 1.28-2.56 | 0.64-1.28 |

FIGURE 4

ANTIMICROBIAL PEPTIDE, COMPOSITIONS, AND USES THEREFOR

This application is a continuation-in-part of application Ser. No. 10/296,853 filed on Feb. 27, 2003, now abandoned which is a national stage application under 35 U.S.C. §371 of international application PCT/BR01/00070 filed on May 29, 2001, which claims priority to Brazil application PI 0001870-8 filed on May 29, 2000, the entire disclosures of which are hereby expressly incorporated by reference.

The invention refers to small peptides with low hemolytic activity, presenting equivalent activity against parasites, fungi and bacteria.

A number of peptides extracted from animals and plants have shown activity against infection. The application PCT WO 95/03325, published on Feb. 2, 1995, mentions peptides called protegrins, also reviewing literature on this subject, which includes references on tachyplesins, poliphemusins, defensins, β-defensins and insect defensins. The U.S. Pat. No. 5,994,306 refers to more specific protegrins.

The application PCT WO 97/02287, published on Jan. 23, 1997, discloses peptides called parevins and tachytegrins, which are similar to protegrins, except for cysteines on positions 6 and 15.

This invention has the object to disclose new and small peptides which are similar in some aspects to protegrins, tachytegrins and parevins, but presenting a balanced anti-parasitic, anti-bacterial and anti-fungal activity, besides low hemolytic activity. This peptide is called gomesin, configured as a hairpin structure consisting of two anti-parallel beta-folded sheets, joined by a beta turn, containing four invariable cysteine residues forming two disulphide bridges, with the following general formula (1):

GENERAL FORMULA (1)

in which:

$Z_1$ is:
in the absence of $X_{19}$, a free amino end residue or a residue with a blocked end amino group by methylation, carbamylation, acylation, acetylation, or some protecting group like tertbutyl, etc, preferably pyroglutamic acid, providing resistance against protease activity;

when $X_{19}$ is present, glutamine with a free amino end group available to close the ends of the molecule;

$P_1$ and $P_2$ are disulphide bridges from $C_2$ to $C_{15}$, and from $C_6$ to $C_{11}$, respectively, either one or both bridges being present;

Y, K, Q, and R in positions 7 to 10 are residues which are able to effect a beta turn;

$R_{18}$ is:
in the absence of $X_{19}$: an arginine bearing a free carboxyl group or forming an acceptable salt such as potassium, sodium, calcium, magnesium or other with an organic or inorganic ion, or amidated with an amine of the formula $NH_3$ or $RNH_2$ or $R_2NH$, in which R is independently a saturated or unsaturated hydrocarbyl with one to six carbons, such as methyl, ethyl, isopropyl, t-butyl, n-pentyl, cyclohexyl, 2-cyclohexenyl, 3-cyclohexenyl, 4-hexinyl and similar;

when $X_{19}$ is present: an arginine which free carboxyl group end is involved with the closing of peptide molecule ends;

$X_{19}$ may be absent or present; if present, it is a chemical link between $Z_1$ and $R_{18}$ or a chemical structure or molecule present between $Z_1$ and $R_{18}$ and linked to both, closing the amino acid chain ends of the peptide of the invention;

The peptides of the invention should present a positive net charge of at least +1 at physiological pH.

According to the present application the term "open ended cyclic peptide" refers to the gomesin with open ends, while the term "head-to-tail cyclic gomesin" refers to the gomesin with closed ends.

The gomesin can be obtained by extraction from animals, such as from the spider *Acanthoscurria gomesiana*. Other peptides of the invention can also be synthetically produced and, when containing only genetically coded amino acids, they can be produced in a recombinant way. Peptides of the invention are useful for the treatment and prevention of animal and plant infection as caused by parasites, bacteria and/or fungi. In another aspect, DNA coding the peptides of the invention may be expressed in situ, in animals or plants, to fight infection. Peptides of the invention can also be used as standard for antimicrobial tests and for binding to endotoxins.

Peptides of the invention can be obtained in a recombinant way by means of peptide-coding cDNA expression in heterologous systems, as well known in the literature.

The invention also refers to useful compositions against bacteria, fungi and parasites, used in the combat against such organisms.

Peptides of the invention are generally different from others known in the art, among other reasons, for presenting the following qualities, which had not been simultaneously found so far:

small structure, therefore prone to be better distributed within tissues and less immunogenic;

about equally active against bacteria, fungi and parasites (while e.g. protegrins are less efficient against fungi);

low hemolytic activity, especially in a head-to-tail cyclic configuration;

Peptides of the invention contain a beta turn connecting two beta-turned sheets. As it is known by one skilled in the art, a beta fold refers typically to a peptide segment containing residues of four amino acids reversing the amino acid chain direction. Cysteines $C_2$, $C_6$, $C_{11}$ and $C_{15}$ provide for the existence of the beta turn by forming disulphide bridges between them, that is, from $C_2$ to $C_{15}$, and from $C_6$ to $C_{11}$.

As known in the literature, disulphide bridges can be substituted by lactam bridges (as shown on FIG. 3) or any other bridge playing an equivalent role.

In an alternative embodiment, peptides of the invention can present a cyclic structure with closed ends in the peptide chain. Methods to obtain head-to-tail cyclic peptides are known in the art.

In open ended cyclic peptides, as known to one skilled in the art, amino and carboxy ends may be derived. In the peptides of the invention, the amino group end may be methylated, carbamylated, acylated, acetylated or be pyroglutamic acid. Peptides of the invention may, by means of addition to the carboxyl end of the molecules, be present as inorganic salts, such as chloride, bromide, iodide, fluoride, sulphate, nitrate, phosphate, etc., or organic salts, such as acetate, formate, benzoate, etc. The acceptance of each one of the above salts depends on the desired use, which is routinely understood. The carboxyl end can also be amidated. Derivation reactions are known.

Figure 3:
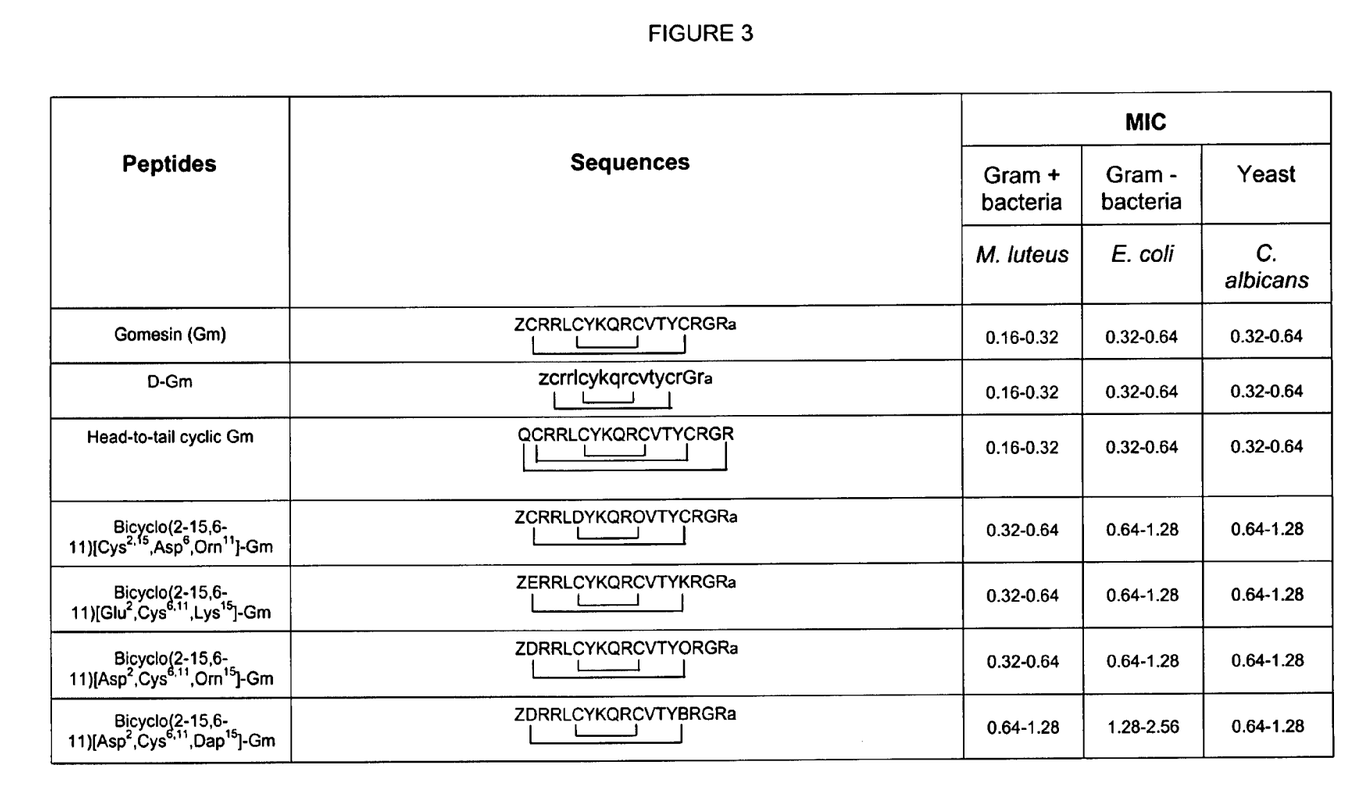
FIG. 3 is a listing of peptides, their sequences with gram + bacteria, gram − bacteria and yeast.

The functional equivalents of the peptides of the invention are also compounds where one or several amino acids are enantiomers, diastereoisomers, and natural amino acids with a D-conformation (as shown on FIG. 3). The invention is also covering synthetic amino acids such as ornithine and 2,3 diaminoproprionic acid (DAP) involved in the lactama bridges—herein represented by O and B, respectively.

According to a particular embodiment, the general formula (1) of the peptides of the invention is as follows:

a) in the absence of $X_{19}$:

$R_{18}$ is preferably an amidated arginine, optionally non-amidated;

b) in the presence of $X_{19}$:

$R_{18}$ has a free carboxyl end group involved in closing peptide ends.

$X_{19}$ is a chemical structure present between $Z_1$ and $R_{18}$, connected to both, so as to close the peptide chain ends.

In particular embodiments, peptides of the present invention present the following sequences:

```
SEQ ID No 1:      ZCRRLCYKQRCVTYCRGR_a
``` in which
Z=pyroglutamic acid
C=cysteine
R=arginine
$R_a$=arginine amidated
L=leucine
Y=tyrosine
K=lysine
Q=glutamine
V=valine
T=threonine
G=glycine, or

```
SEQ ID No 2:      ZCRRLCYKQRCVTYCRGR
``` in which the amino acids are as described above and a head to tail cyclic peptide

```
SEQ ID No 3:      QCRRLCYKQRCVTYCRGR
``` in which the amino acids are as described above.

EXAMPLES OF PROCESSES TO OBTAIN THE PEPTIDES OF THE INVENTION

The examples given herein are intended to explain the invention, and do not add any limitation to the claims that follow at the end of this specification.

Example 1

Extraction of Gomesin from the Spider *Acanthoscurria gomesiana*

By means of the process described below, a gomesin corresponding specifically to the following structure within the general formula (1) was obtained, including two disulphide bridges (representation just for illustrative purposes):

in which:
Z=pyroglutamic acid
C=cysteine
R=arginine
L=leucine
Y=tyrosine
K=lysine
Q=glutamine
V=valine
T=threonine
G=glycine
$R_a$=arginine with "a" that stands for an amidated carboxyl group end Hemolymph (approximately 0.4 ml/spider) from both male and female animals in different development stages was collected, from pre-cooled animals by heart puncture with an apyrogenic syringe, in the presence of sodium citrate buffer (30 mmol/L, pH 4.6) containing NaCl (450 mmol/L), EDTA (10 mmol/L) and glucose (100 mmol/L). Hemocytes were removed from the plasma by centrifugation at 800×g for 10 minutes at 4° C. Entire hemocytes were washed once with sodium citrate buffer and lysated by concentration in a vacuum centrifuge.

After concentration, hemocytes were re-suspended in a 1.5 ml of 2M acetic acid supplemented with aprotinin (20 μg/ml) as protease inhibitor, being homogenized in a Dounce equipment (maximum 152μ, minimum 76μ). A second homogenization was effected by means of sonication (3×30 s) at average intensity, kept in an ice cold water bath and the extraction was effected for 30 minutes at 4° C. under mild stirring. The supernatant obtained by means of centrifugation at 13,800×g for 30 minutes at 6° C. was directly submitted to pre-purification by solid phase extraction.

Organella and cytosolic acid extracts were applied to solid phase columns connected in series, equilibrated in acidic water (0.05% trifluoroacetic acid). Three elutions were successively effected with 5%, 40% and 80% acetonitrile in acidic water. The 40% acetonitrile portion was concentrated by centrifugation under vacuum, reconstituted with MiliQ water and reverse phase chromatographed in a column equilibrated with 2% acetonitrile in acidified water. Elution was performed with a linear gradient of acetonitrile from 2 to 60% in acidified water for 120 minutes, at a flow rate of 1.3 ml/min.

The active fraction against the tested bacterium *Micrococcus luteus* of hemocytes (AGH2) is additionally purified by filtration chromatography. Elution is made under isocratic conditions with 30% acetonitrile in acidic water at a flow rate of 0.4 ml/min. HPLC (high performance liquid chromatography) purification was made at room temperature. The effluent column was monitored for its absorbance at 225 nm. Fractions corresponding to absorbance peaks were collected, concentrated under vacuum and reconstituted in MilliQ water. Anti-bacterial activity of the collected fractions was monitored by a liquid growth inhibition assay according to J. Biol. Chem., 268, 14893-14897 (1993), using *Micrococcus luteus* as the test microorganism.

Example 2

Gomesin Synthesis

Peptides of the invention were synthesized using a classic Fmoc procedure as described in J. Biol. Chem., 271, 29537-29544 (1996).

For comparison with the gomesin obtained by extraction, as mentioned before, the following peptide was synthesized:

$R_a$ stands for a C-terminal arginine residue with an α-amide group

Figure 1:
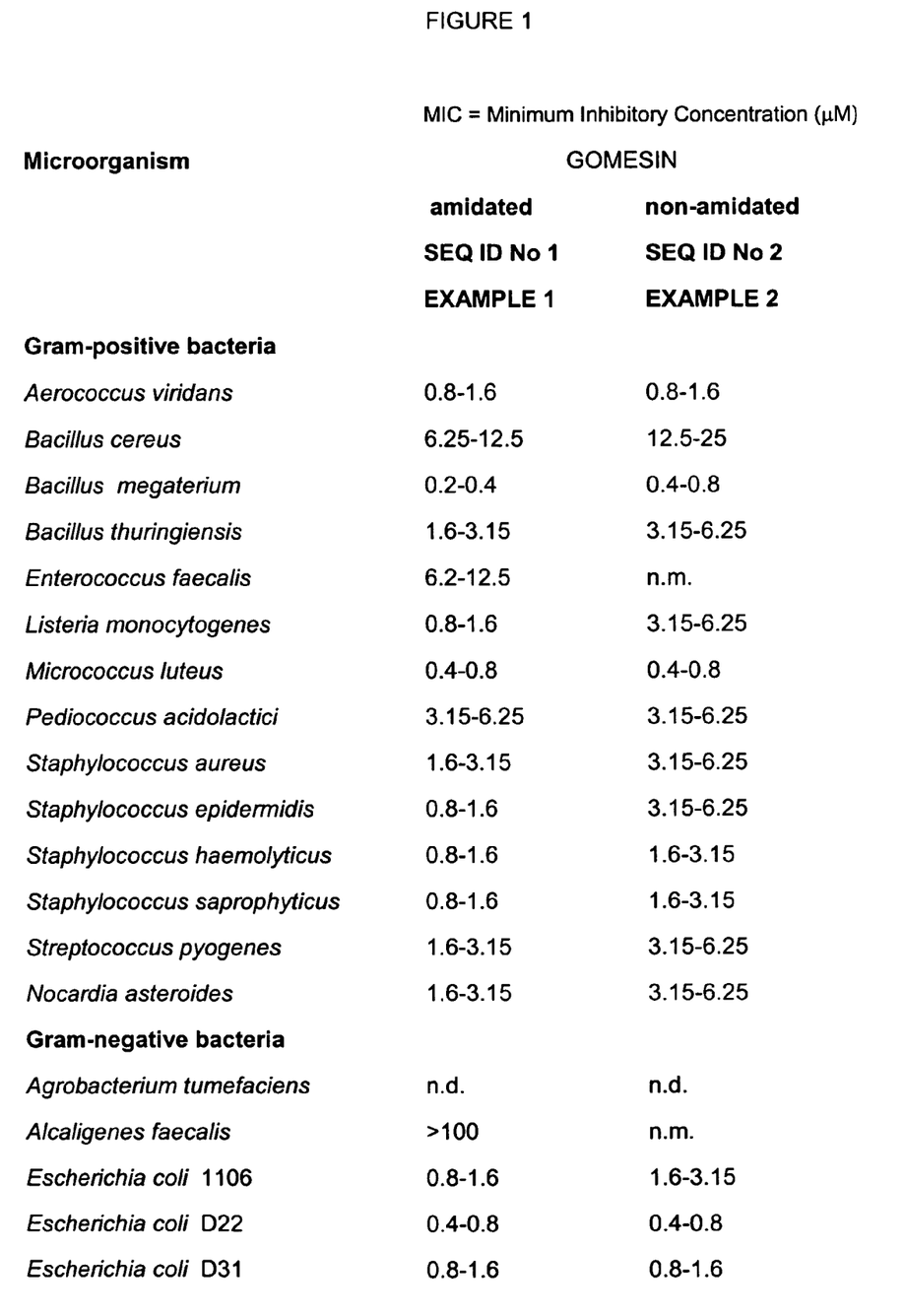
FIG. 1 is a listing that shows the activity spectrum for amidated gomesin and its non-amidated version against bacteria, fungi and yeast.

FIG. 1 attached shows the activity spectrum for amidated gomesin (Example 1) and its non-amidated version (Example 2), against bacteria, fungi and yeast. The evaluation of activity against bacteria and fungi was done as described in J. Biol. Chem., 271, 29537-29544 (1996).

On FIG. 1, n.d. means "non-detected" for the tested concentration range of up to 100 µM for gomesin, while n.m. means not measured. The minimal inhibitory concentrations (MICs) of synthetic peptides are expressed as the [A]-[B] interval of concentrations, where [A] is the highest concentration tested at which the microorganisms are growing and [B] is the lowest concentration that causes 100% growth inhibition.

Figure 2:
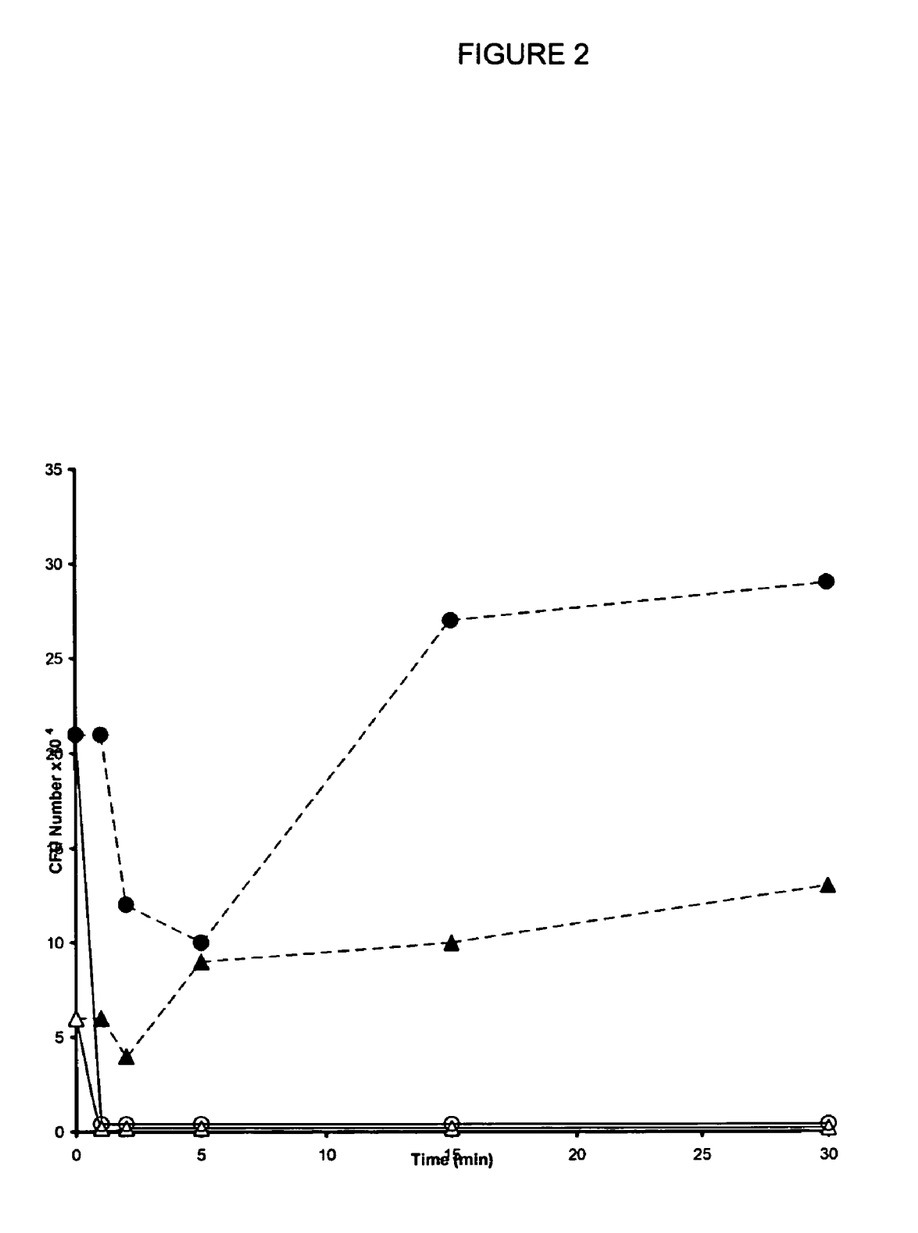
FIG. 2 is a graph that illustrates the anti-bacterial properties for the peptides of claim 1 by the mortality of *Micrococcus luteus* and *Escherichia coli* D22.

Said FIG. 1 shows that the peptide of the invention has anti-bacterial properties. As shown, gomesin (from Example 1 above) is effective against most tested strains, with 24 from the 27 strains being susceptible to gomesin under MIC (minimum inhibitory concentration) below or equal to 1.6 µM for half of them, under concentrations from 1.6 to 6.25 µM for 42% of them. Anti-bacterial properties were also verified for the peptides of the invention, e.g. by the mortality of *Micrococcus luteus* and *Escherichia coli* D22 as shown in FIG. 2. 10 µM of the gomesin of Example 1 (solid line) or water (dotted line) were added to an exponential stage culture of *M. luteus* (circles) or *E. coli* (triangles). Aliquotes were removed at different time intervals and the number of CFU (colony forming units) counted by plating on Luria Bertani agar plates after overnight incubation at 37° C. The kinetic of killing of gomesin, as shown after approximately one minute, is one of the advantages of the invention.

Example 3

Antimicrobial Activity of Head-To-Tail Cyclic Gomesin

The antimicrobial activity of the head-to-tail cyclic gomesin peptide (SEQ ID No 3) was evaluated using the same assay described above. The data as presented on the FIG. 3, show that the head-to-tail cyclic gomesin of the invention exhibited antimicrobial activity against the tested Gram-positive and Gram-negative bacteria and yeast, identical to the activity of native gomesin.

Example 4

Anti-Parasitic Activity

As an example of anti-parasitic activity, the cell viability of *Leishmania (leishmania) amazonensis* (MRPO/BR/72/M 1841-LV-79) and *Trypanosoma cruzi* were evaluated, by making use of the MTT [3-(4,5-dimethyltiazolyl-2)-2,5-diphenyl tetrazolio bromide] test as described in J. Immunol. Methods 65, 55-63 (1983) and adapted for *Leishmania* spp, according to J. Immunol. Methods 127, 11-18 (1990).

Figure 4:
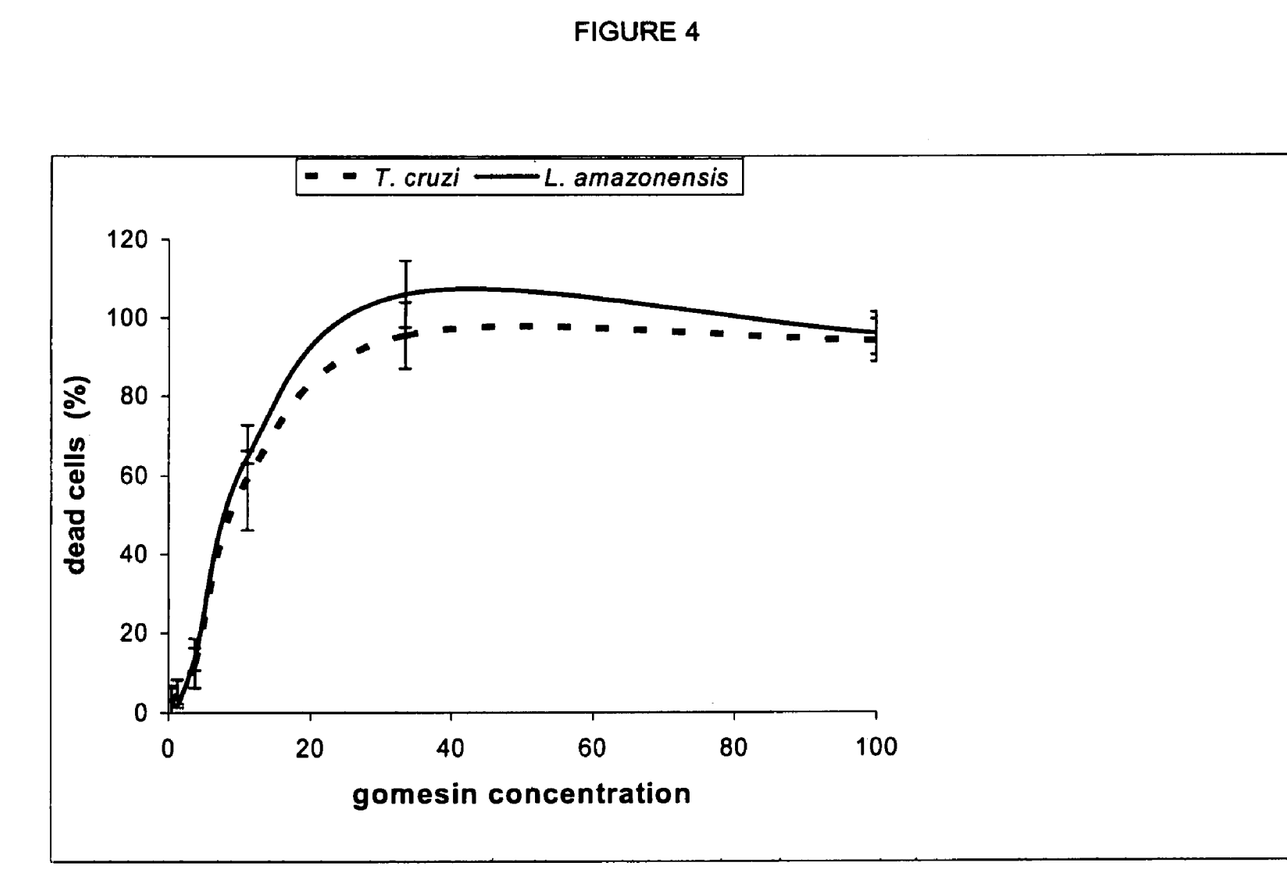
FIG. 4 is a graph of percent of dead cells with gomesin concentration.

Quantities from 0.1 to 100 µM were tested against *Leishmania (leishmania) amazonensis* and *Trypanosoma cruzi*. After incubation for one hour, the viability of parasites was noticed as dependent on the concentration of gomesin, as shown in FIG. 4. FIG. 4 shows as solid line, *T. Cruzi* incubated with synthetic gomesin (SEQ ID No 1) and as hatched line, *L. amazonensis* incubated with the same peptide for one hour at 22° C. under concentrations from 0.1 to 100 µM. The death of parasites (%) was measured by making use of the MTT assay as described in J. Immunol. Methods 65, 55-63 (1983) and adapted for *Leishmania* spp, according to J. Immunol. Methods 127, 11-18 (1990).

Peptides of the invention may be used in various compositions, which are active against bacteria, fungi and parasites. They can be used individually, or with other microbicidal agents, and jointly with other ingredients known in the art, e.g. active principles such as erythromycin, tetracycline, azithromicin, cephalosporins, etc. and general constituents such as carriers, diluents, excipients, etc.

Peptides of the invention may be formulated for pharmaceutical, botanical or veterinary use.

The compositions of the invention can be presented in any form, adapted to the intended purpose as well known by a person skilled in the art, e.g. for topic use such as creams, oils, ointments, powders, gels, etc. or appropriately for oral, transdermal, transmucous, intramuscular, intravenous, subcutaneous, etc. administration.

The invention claimed is:

1. An isolated peptide of the general formula:

in which: $Z_1$ is:
- in the absence of $X_{19}$, pyroglutamic acid;
- when $X_{19}$ is present, glutamine with a free amino end group available to close the ends of the molecule;

$P_1$ and $P_2$ are disulphide bridges from $C_2$ to $C_{15}$ and from $C_6$ to $C_{11}$, respectively, either one or both bridges being present;

$R_{18}$ is:
- in the absence of $X_{19}$: an arginine bearing a free carboxyl group end or forming an acceptable salt, or amidated with an amine of the formula $NH_3$ or $RNH_2$ or $R_2NH$, in which R is independently a saturated or unsaturated hydrocarbyl with one to six carbons;
- when $X_{19}$ is present: an arginine whose free carboxyl end is involved with the closing of peptide molecule ends;

$X_{19}$ may be absent or present; if present, it is a chemical link between $Z_1$ and $R_{18}$ or a chemical structure or molecule present between $Z_1$ and $R_{18}$ and linked to both, closing the amino acid chain ends of the peptide of the invention, wherein, in the absence of $X_{19}$, $R_{18}$, said peptide is amidated (SEQ ID NO: 1).

2. The peptide of claim 1 in which, when $X_{19}$ is present $R_{18}$ is non-amidated (SEQ ID NO: 2).

3. The peptide of claim 1 in which, when $X_{19}$ is present $R_{18}$ is non-amidated and $Z_1$ is Q (SEQ ID NO: 3).

4. A pharmaceutical, botanical or veterinary composition comprising the peptide of claim 1 in admixture with at least one carrier, diluent, or excipient.

5. A method for treating an infection associated with a human, animal or plant disease, said disease being selected from the group consisting of a bacterial infection, a fungal infection, a yeast infection and a parasitic infection, comprising administering to said human, animal or plant an effective amount of the peptide of any one of claims 1, 2 and 3.

6. A method for treating an infection associated with a human, animal or plant disease, said disease being selected from the group consisting of a bacterial infection, a fungal infection, a yeast infection and a parasitic infection, comprising administering to said human, animal or plant the composition of claim 4.

7. A method of inhibiting the development of parasites, fungi or bacteria associated with an infection, comprising contacting said parasites, fungi or bacteria with an effective amount of a peptide of any one of claims 1, 2 and 3.

8. The method of claim 7, in which the parasite is a protozoary.

9. The method of claim 7, in which the parasite is a *Leishmania* or *T. cruzi*.

10. A method to inactivate the endotoxin from Gram-negative bacteria, in which said endotoxin is contacted with an amount of a peptide of any one of claims 1, 2 and 4, which is effective to inactivate said endotoxin.

* * * * *

SEQUENCE LISTING

<160> NUMBER OF SEQ ID NOS: 7

<210> SEQ ID NO 1
<211> LENGTH: 18

```
<212> TYPE: PRT
<213> ORGANISM: Artificial Sequence
<220> FEATURE:
<223> OTHER INFORMATION: Synthesized Sequence
<220> FEATURE:
<221> NAME/KEY: VARIANT
<222> LOCATION: 1
<223> OTHER INFORMATION: Xaa = Pyroglutamic Acid
<220> FEATURE:
<221> NAME/KEY: VARIANT
<222> LOCATION: 18
<223> OTHER INFORMATION: Xaa = Arginine amidated

<400> SEQUENCE: 1

Xaa Cys Arg Arg Leu Cys Tyr Lys Gln Arg Cys Val Thr Tyr Cys Arg
 1               5                  10                  15

Gly Xaa

<210> SEQ ID NO 2
<211> LENGTH: 18
<212> TYPE: PRT
<213> ORGANISM: Acanthoscurria gomesiana
<220> FEATURE:
<221> NAME/KEY: VARIANT
<222> LOCATION: 1
<223> OTHER INFORMATION: Xaa = Pyroglutamic Acid

<400> SEQUENCE: 2

Xaa Cys Arg Arg Leu Cys Tyr Lys Gln Arg Cys Val Thr Tyr Cys Arg
 1               5                  10                  15

Gly Arg

<210> SEQ ID NO 3
<211> LENGTH: 18
<212> TYPE: PRT
<213> ORGANISM: Artificial Sequence
<220> FEATURE:
<223> OTHER INFORMATION: Synthesized Sequence

<400> SEQUENCE: 3

Gln Cys Arg Arg Leu Cys Tyr Lys Gln Arg Cys Val Thr Tyr Cys Arg
 1               5                  10                  15

Gly Arg

<210> SEQ ID NO 4
<211> LENGTH: 18
<212> TYPE: PRT
<213> ORGANISM: Artificial Sequence
<220> FEATURE:
<223> OTHER INFORMATION: Synthesized sequence
<220> FEATURE:
<221> NAME/KEY: VARIANT
<222> LOCATION: 1
<223> OTHER INFORMATION: Xaa = Pyroglutamic acid
<220> FEATURE:
<221> NAME/KEY: VARIANT
<222> LOCATION: 11
<223> OTHER INFORMATION: Xaa = Ornithine
<220> FEATURE:
<221> NAME/KEY: VARIANT
<222> LOCATION: 18
<223> OTHER INFORMATION: Xaa = Arginine amidated

<400> SEQUENCE: 4

Xaa Cys Arg Arg Leu Asp Tyr Lys Gln Arg Xaa Val Thr Tyr Cys Arg
 1               5                  10                  15

Gly Xaa
```

-continued

```
<210> SEQ ID NO 5
<211> LENGTH: 18
<212> TYPE: PRT
<213> ORGANISM: Artificial Sequence
<220> FEATURE:
<223> OTHER INFORMATION: Synthesized sequence
<220> FEATURE:
<221> NAME/KEY: VARIANT
<222> LOCATION: 1
<223> OTHER INFORMATION: Xaa = Pyroglutamic acid
<220> FEATURE:
<221> NAME/KEY: VARIANT
<222> LOCATION: 18
<223> OTHER INFORMATION: Xaa = Arginine amidated

<400> SEQUENCE: 5

Xaa Glu Arg Arg Leu Cys Tyr Lys Gln Arg Cys Val Thr Tyr Lys Arg
 1               5                  10                  15

Gly Xaa

<210> SEQ ID NO 6
<211> LENGTH: 18
<212> TYPE: PRT
<213> ORGANISM: Artificial Sequence
<220> FEATURE:
<223> OTHER INFORMATION: Synthesized sequence
<220> FEATURE:
<221> NAME/KEY: VARIANT
<222> LOCATION: 1
<223> OTHER INFORMATION: Xaa = Pyroglutamic acid
<220> FEATURE:
<221> NAME/KEY: VARIANT
<222> LOCATION: 15
<223> OTHER INFORMATION: Xaa = Ornithine
<220> FEATURE:
<221> NAME/KEY: VARIANT
<222> LOCATION: 18
<223> OTHER INFORMATION: Xaa = Arginine amidated

<400> SEQUENCE: 6

Xaa Asp Arg Arg Leu Cys Tyr Lys Gln Arg Cys Val Thr Tyr Xaa Arg
 1               5                  10                  15

Gly Xaa

<210> SEQ ID NO 7
<211> LENGTH: 18
<212> TYPE: PRT
<213> ORGANISM: Artificial Sequence
<220> FEATURE:
<223> OTHER INFORMATION: Synthesized sequence
<220> FEATURE:
<221> NAME/KEY: VARIANT
<222> LOCATION: 1
<223> OTHER INFORMATION: Xaa = Pyroglutamic acid
<220> FEATURE:
<221> NAME/KEY: VARIANT
<222> LOCATION: 15
<223> OTHER INFORMATION: Xaa = Diaminoproprionic acid
<220> FEATURE:
<221> NAME/KEY: VARIANT
<222> LOCATION: 18
<223> OTHER INFORMATION: Xaa = Arginine amidated

<400> SEQUENCE: 7

Xaa Asp Arg Arg Leu Cys Tyr Lys Gln Arg Cys Val Thr Tyr Xaa Arg
 1               5                  10                  15

Gly Xaa
```